US006632906B1

(12) United States Patent
Kamiyama

(10) Patent No.: US 6,632,906 B1
(45) Date of Patent: Oct. 14, 2003

(54) ADHESIVES

(75) Inventor: Fumio Kamiyama, Wakiyama (JP)

(73) Assignee: Strakan Limited, Hamilton (BM)

( * ) Notice: Subject to any disclaimer, the term of this patent is extended or adjusted under 35 U.S.C. 154(b) by 0 days.

(21) Appl. No.: 09/890,293

(22) PCT Filed: Jan. 31, 2000

(86) PCT No.: PCT/GB00/00273

§ 371 (c)(1),
(2), (4) Date: Oct. 15, 2001

(87) PCT Pub. No.: WO00/44846

PCT Pub. Date: Aug. 3, 2000

(30) Foreign Application Priority Data

Jan. 29, 1999 (GB) ................................................ 9902063
Nov. 25, 1999 (GB) ................................................ 9927922

(51) Int. Cl.[7] ........................ C08F 116/36; C08F 118/02
(52) U.S. Cl. ........................ 526/316; 526/319; 526/347; 524/282
(58) Field of Search ............................... 526/316, 303.1, 526/347, 319, 217; 524/282

(56) References Cited

U.S. PATENT DOCUMENTS

| 3,293,215 A | 12/1966 | Loral |
| 4,737,559 A | 4/1988 | Kellen et al. |
| 4,987,186 A | 1/1991 | Akiyama et al. |
| 5,872,160 A * | 2/1999 | Liang et al. ................. 528/120 |

FOREIGN PATENT DOCUMENTS

| DE | 25 55 729 A1 * | 6/1977 |
| GB | 1 133 410 A | 11/1968 |
| WO | 0 778 317 A2 | 6/1997 |
| WO | WO 97/43325 | 11/1997 |

* cited by examiner

*Primary Examiner*—Robert Harlan
(74) *Attorney, Agent, or Firm*—Fish & Richardson P.C.

(57) ABSTRACT

An adhesive material is suitable as a bioadhesive and comprises an adhesive polymer and a plasticizier thereof, wherein the adhesive is cross-linked, characterized in that the adhesive comprises ketone groups cross-linked by a polyamine cross-linking agent. Such adhesives have good cohesion and low dermal irritation.

28 Claims, No Drawings

ADHESIVES

The present invention relates to adhesives suitable for use as bioadhesives and which comprise both adhesive polymer and plasticiser.

Various applications for bioadhesives exist, including medical tape and transdermal patches, for example. Methods of manufacture of these products are well advanced, but the nature of the adhesive remains a problem.

If the adhesive on medical tape is too strong, then removal can be painful, and will also serve to exfoliate the skin, which can cause irritation and may even lead to sensitisation to any drugs that the patient might be taking.

If the bioadhesive is too weak, then the patch or tape will tend to come away from the skin before it should. This has led to bioadhesives being developed which have merely been adapted so as not to be too strong to be painful, and not so weak as to be relatively useless.

More recently, it has been established that strong adhesives can be tempered with plasticisers. These generally take the form of oil substances introduced into the adhesive polymer. The effect of the introduction of such oily substances is to soften the physical structure of the adhesive whilst, at the same time, acting at the interface between the adhesive and the skin, thereby helping to somewhat weaken the adhesive, and to prevent exfoliation. Such a beneficial type of adhesive was first noted in certain types of electrical insulating tape.

The problem with such softened, or plasticised, adhesives is that, once they are weak enough to be medically acceptable, their cohesive strength is poor. Thus, such adhesives, when used in transdermal patches or surgical tape, for example, have insufficient integrity, and tend to tear, leaving bits of adhesive behind on the skin.

EP-A-450986 discloses an acrylic adhesive plasticised with isopropyl myristate (IPM) and which also contains nitroglycerine, which can further serve as a plasticiser. In order to improve cohesion of this adhesive, cross-linking was effected with aerosil silica. The problem with such cross-linking is the technical difficulty involved in sufficiently finely dividing the aerosil silica and incorporating it uniformly throughout the adhesive. Such cross-linking would not be generally practical.

U.S. Pat. No. 5,298,258 more generally seeks to solve the problems noted above, and discloses acrylic adhesives containing substantial amounts of plasticisers. Various methods for cross-linking the adhesive are mentioned, including irradiation and exposure to UV, but chemical cross-linking with a metal alcoholate, metal chelate or trifunctional isocyanate is preferred. The cross-linking of such an adhesive requires the presence of active hydrogen, generally in the form of a carboxyl or hydroxyl group, typically provided by a co-monomer having the required functionality.

The problem with such a system is with regard to the nature of the cross-linking, where there is necessarily involved an active chemical reagent, either on the adhesive (carboxyl groups, for example) or in the cross-linker (such as aluminium in aluminium alcoholate). Many drugs can react or interact with such groups, which can lead to problems, such as breakdown of the drug, or simple blocking of the cross-linking. For example, where a drug is weakly basic, then this can interact with the carboxyl groups present on the adhesive, thereby competing with the cross-linker.

WO 99/02141 discloses block copolymers wherein the soft segments are cross-linked, these copolymers being suitable for use as drug-retaining bioadhesives in transdermal patches. These adhesives suffer a loss of cohesion, however, when a plasticiser is incorporated.

It has now, surprisingly, been found that it is possible to provide a satisfactory medical adhesive with good cohesion and adhesion properties and low irritation which comprises an adhesive polymer and a plasticiser, wherein the polymer is cross-linked by a polyamine reacting with ketone groups present in the adhesive. Such adhesives are also useful in other non-medical applications where it is desired to apply an area of material, such as a patch or tape, for what may be only a limited period of time.

Thus, in a first aspect, the present invention provides an adhesive material suitable for use as a bioadhesive and comprising an adhesive polymer and a plasticiser therefor, wherein the adhesive is cross-linked, characterised in that the adhesive comprises ketone groups cross-linked by a polyamine cross-linking agent.

For the avoidance of doubt, the present invention encompasses novel adhesive materials, as disclosed herein, wherein the polymer and/or copolymer constituents thereof are cross-linked, wherein at least a portion of the cross links comprise a moiety

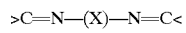

in which the carbon atoms are each a part of the respective polymer and/or copolymer constituents and each X is the same or different, preferably the same, and is directly equivalent to any group that would serve to carry the necessary amine groups of a polyamine cross-linking agent of the present invention.

Accordingly, it will be appreciated that X need not necessarily exist, in the instance of hydrazine, for example. It will also be appreciated that more than two suitable amine groups may be attached to X, although X may often be of the form $X^1$—N<, or of the form $X^2(NA-)_2$, wherein $X^1$ and $X^2$ represent the kernel of X, and the groups —N< and NA represent the links with —N=C< groups, with each A representing a hydrogen or a direct bond with $X^2$.

Bioadhesive materials of the present invention have been found to possess good water vapour permeabilities, which allows the skin to breathe when the tape or patch is in place. In addition, the lack of any necessary reactive groups is useful for drug stability, and also in providing certain sorts of patch that could not previously be made, as the bioadhesives of the invention are generally susceptible to very little interaction with other materials.

It will be appreciated that the adhesive polymers of the present invention are not restricted to the nature of the application, and that any reference to a specific embodiment, such as tape, or a patch, should be construed as incorporating reference to any other possible embodiment incorporating an adhesive of the invention, mutatis mutandis, where appropriate.

The nature of the adhesive polymer is not critical to the present invention. Indeed, the term "polymer" is used generically herein to relate to polymers, copolymers and mixtures thereof.

In general, it is preferred that the polymer should be a synthetic polymer, in order to be able to provide adequate quality control and predictability of results. It is also advantageous to use synthetic polymers, as they can be controlled to contain desired side-groups, as necessary. In the present invention, the adhesive polymer, or a substantial component thereof, has at least one ketone group which is able to react with a polyamine.

Ketone groups are capable of tautomerisation, where there is an equilibrium between the ketone and the corresponding enol compound. This equilibrium is generally in favour of the ketone. In the present invention, it is strongly preferred that the ketone-containing polymer should have at least one ketone group with little or substantially no tendency to enolisation. Hence, it is preferred that the ketone group should not be part of a larger functionality, and it is particularly the case that the ketone group should not be part of a carboxyl group or any derivative thereof, such as an esteric linkage or amide group, although it may be linked to or adjacent such a group. It is also strongly preferred that the ketone group should not be part of an aldehyde group.

It appears that, in the present invention, the cross-linking reaction takes place between the keto form of the carbonyl group and the amine group of the cross-linking agent. It has been found that, if the ketone group is not stable in the keto form, then it reacts only poorly, if at all, with the cross-linking agent. Preferred compounds are those in which the keto form is at least 100 fold more stable than the enol form, preferably more stable by a factor of $10^4$, most preferably more stable by a factor of $10^6$ or greater. Preferably the equilibrium constant K (enol/keto), when measured in water, is less than $10^{-2}$, more preferably less than $10^{-4}$, and most preferably less than $10^{-6}$, or even smaller. In this way, the equilibrium is strongly biased in favour of the keto form. Other factors aside, the more strongly biased the equilibrium toward the ketone group, the better.

Given the preference for the ketone group to not readily be able to form an enol group, then it will be appreciated that functionalities in the proximity of the reactive ketone group are preferred which do not encourage the keto group to enolise. In fact, such functionalities are preferred where stabilisation of the keto group is encouraged.

Block copolymers are useful in the present invention. Suitable block copolymers consist of a mixture of 'hard' (A) and 'soft' (B) segments, which may be combined in an A-B-A or $(A-B)_n$ type structure (c.f. Block Copolymers: Overview and Critical Survey, Noshay and McGrath, 1977). Association of the hard segments is thought to provide a degree of physical cross-linking, which improves the cohesive properties of the adhesive. Acrylic block copolymers, comprising soft and hard segments, having a degree of chemical cross-linking between the soft segments, are preferred.

More specifically, the term 'block copolymer', as used herein, refers to a macromolecule comprised of two, or more, chemically dissimilar polymer structures, terminally connected (Noshay and McGrath, supra). These dissimilar polymer structures, sections or segments, represent the 'blocks' of the block copolymer, the A and B segments comprising the chemically distinct polymer segments of the block copolymer. In the present invention, the A-B-A structure is preferred.

In general, it is preferred that the adhesive possesses a minimum number of functionalities having active hydrogen, in order to avoid undesirable reactions/interactions, such as with any drug that it is desired to incorporate into the bioadhesive material. It will be appreciated that this is only a preferred restriction, and that any adhesive may be tailored by one skilled in the art to suit individual requirements. For example, it may be desirable to incorporate certain active groups into the adhesive in order to encourage uptake of a given compound, such as a drug. It is also the case that, where the adhesive is not intended for medical use, restrictions on any medically undesirable function are not so severe. Where the adhesive is used as an adhesive in its own right, without carrying a drug, such as in medical or surgical tape, then it is also less of a requirement to limit active functionalities, although limiting such functionalities generally helps to reduce irritation and, so, is preferred.

Limiting active functionalities, especially those with active hydrogen, is generally preferred, in order to permit wide use of any given formulation of adhesive without having to take into account how it is likely to interact, chemically, with its environment. However, as stated above, an adhesive required for any individual purpose may be tailored as seen fit by one skilled in the art. Thus, a generally chemically inert adhesive is preferred, in the absence of requirements to the contrary.

It will be appreciated that the term 'drug', as used herein, refers to any substance or compound suitable for administration via the adhesive of the invention, typically a transdermal patch. A substance having drug retention properties is taken herein as being a substance capable of absorbing or adsorbing a drug. In the instance where the substance is loaded with drug for dispensing via a transdermal patch, then it will be appreciated that such absorbance and/or adsorbance should be at least partially reversible.

Adhesives of the present invention are particularly of use in medical and veterinary applications, although the latter may tend to suffer from the disadvantage of the animal endeavouring to remove the dressing or tape. Tapes employing the adhesives of the invention exhibit good adhesion and cohesion, and release freely from the subject without painful exfoliation. It will be appreciated that, while tapes will not necessarily carry drugs, it may be beneficial for a tape to carry such agents as antimicrobial agents.

Preferred adhesives of the invention are those which, in tests, can be applied to newspaper and readily removed therefrom without tearing the paper. Particularly preferred are those adhesives which can be removed from, and reapplied to, newspaper repeatedly, without losing adhesion or damaging the paper. Tapes having such properties are particularly useful, and are preferred embodiments of the present invention.

Suitable examples of drug-impermeable backings which may be used for transdermal patches include films or sheets of polyolefins, polyesters, polyurethanes, polyvinyl alcohols, polyvinyl chlorides, polyvinylidene chloride, polyamides, ethylene-vinyl acetate copolymer (EVA), ethylene-ethylacrylate copolymer (EEA), vinyl acetate-vinyl chloride copolymer, cellulose acetate, ethyl cellulose, metal vapour deposited films or sheets thereof, rubber sheets or films, expanded synthetic resin sheets or films, nonwoven fabrics, fabrics, knitted fabrics, paper and foils. Other backings will be readily apparent to those skilled in the art.

Breathability is important, and it is generally preferred that, while the backing material is strong, it should also be able to allow the passage of water vapour, at least in medical applications. In the case of transdermal patches, water vapour permeability can be tempered by the requirement for drug-impermeability.

Adhesives of the present invention are also particularly useful in the construction of patches for transdermal delivery of drugs. It will be readily apparent to those skilled in the art which adhesives will be suitable for this purpose, and examples are given below. A highly preferred type of adhesive corresponds to those disclosed in WO 99/02141 (supra), incorporated herein in its entirety. Where the adhesive does not already possess a suitable ketone group, this can readily be provided by the incorporation of a suitable monomer when preparing the polymer. The adhesives of WO 99/02141 already possess good cohesion and adhesion, but addition of plasticiser compromises cohesion. Cross-linking in accordance with the present invention enables the use of these adhesives, retaining their superior drug retention properties and allowing control of the level of adhesion, while allowing painless and irritation-free removal of the patch.

Other applications of the adhesives of the present invention include adhesive tapes for temporarily securing the tape or another object to a delicate surface. Adhesion is good, yet removal of the tape may be readily performed without damaging the delicate surface. The adhesive may also be used for jotter-type applications, for example, where a suitable writing surface, such as paper or plastic, can be temporarily fixed to any surface. Using the adhesives of the present invention means that the user does not have to be concerned where the jotter note is stuck, as removal is easy without damage to any conventional surface.

Many adhesives are known, and it will be apparent to those skilled in the art which adhesives will be useful in the present invention. In general, those based on acrylates and methacrylates are preferred and alkyl acrylates and alkyl methacrylates provide properties of tack and adhesion. Suitable alkyl acrylates and alkyl methacrylates include n-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecyl acrylate and tridecyl methacrylate, although other suitable acrylates and methacrylates will be readily apparent to those skilled in the art. Acrylate block copolymers are suitably used in the present invention, and it is preferred that the acrylic block copolymer comprises at least 50% by weight of alkyl acrylate or alkyl methacrylate (co) polymer.

Particularly where the adhesive is for use in a transdermal patch, it is often preferred that a polar monomer is copolymerised with an alkyl acrylate or alkyl methacrylate, in order to enhance the solubility of certain drugs. Suitable such polar monomers include hydroxyethyl acrylate, hydroxypropyl acrylate, vinyl pyrrolidone, acrylamide, dimethylacrylamide, acrylonitrile, diacetone acrylamide and vinyl acetate.

Diacetone acrylamide, or a combination of diacetone acrylamide and vinyl acetate, is useful in the present invention. The diacetone acrylamide component enables more advantageous drug loading capabilities than vinyl acetate, but vinyl acetate enhances the rate of polymerisation, which is of commercial importance. In such a case, where two polar monomers are used in an adhesive, it will be appreciated that the levels of each monomer may be manipulated in such a way as to provide optimum drug retention and delivery.

Where used, it is preferred that diacetone acrylamide, or other polar monomer, such as hydroxyethyl methacrylate or vinyl acetate, be present in no more than 50% w/w of the monomeric mix, as this can lead to reduced adhesion, for example. However, where adhesion is not important, good levels of drug loading may be obtained with an excess of polar monomer.

In general, it is preferred to provide the adhesive in the form of a copolymer. In the preferred block copolymers, it is preferred that at least the soft segment should be a copolymer. This not only has the advantage of giving a greater variety of polymers from which to select, but is also useful in providing the necessary ketone groups. Suitable monomers (comonomers) will be readily apparent to those skilled in the art and, essentially, are only otherwise limited to compounds which are copolymerisable in the system of choice and which provide the necessary ketone group.

Examples of suitable ketone-providing monomers include aliphatic, olefinically unsaturated keto, preferably monoketo, compounds such as vinyl esters of allyl esters of aliphatic monobasic or dibasic acids containing a keto group and having a suitable number of carbon atoms, such as three to eight. Suitable such acids include pyruvic acid, acetoacetic acid and levulinic acid, a suitable ester of such being the vinyl alcohol ester. For example, one suitable compound, pyruvic acid vinyl alcohol ester, has the formula $H_2C=CH—O—CO—CO—CH_3$.

Other suitable compounds include aliphatic amides substituted at the nitrogen by a vinyl or allyl group and other suitable monomers are the olefinically unsaturated ketones, such as vinylmethyl ketone and vinylethyl ketone. However, the currently preferred monomer is diacetone acrylamide, which is readily commercially available and which has the structure $CH_2=CH—CONH—C(CH_3)_2—CH_2—COCH_3$. A particularly preferred embodiment of the adhesive of the present invention uses a combination of butyl acrylate, 2-ethylhexyl acrylate and diacetone acrylamide, preferably in a ratio of about 4:4:3, either as the adhesive, or as the soft segment of the block copolymer, although other suitable preparations will be apparent to those skilled in the art. In general, unless otherwise specified, ratios and percentages, as given herein, are by weight.

The present invention is not limited to specific plasticisers. The only requirement for the plasticisers is that it be appropriate to the adhesive. For example, using the preferred adhesive noted above, naturally occurring castor oil has been found not to be appropriate, for example, as it leaks out of the adhesive, thereby preventing adhesion. However, appropriate plasticisers are readily established by those skilled in the art. In particular, a simple mixture of a plasticiser with the adhesive should provide a bioadhesive material, or material suitable for use as a bioadhesive (which expressions are used interchangeably herein), which does not separate, and which is adhesive, within the broad general ranges that have generally been noted. Too little plasticiser will generally result in an adhesive material which is too strong and insufficiently soft, while too much plasticiser will generally lead to disruption of the adhesive and permit insufficient adhesive quality.

In general, the plasticiser may be used in an amount generally between about 20 and 200% of the adhesive, more specifically between about 40% and 160%, preferably between about 60 and 120%, with about 100% generally providing good results. It will be appreciated, however, that different plasticisers will have different optima for different adhesives.

Plasticisers are generally liquids having high boiling points, and suitable examples include glycols, such as ethylene glycol, diethylene glycol, triethylene glycol, propylene glycol, polyethylene glycol and polypropylene glycol; fats and oils such as olive oil, castor oil, squalene and lanolin; organic solvents such as dimethyl decyl sulphoxide, methyl octyl sulphoxide, dimethyl sulphoxide, dimethylformamide, dimethylacetamide, dimethyllaurylamide, dodecyl pyrrolidone and isosorbitol; liquid surfactants; specific plasticisers such as diisopropyl adipate, phthalates and diethyl sebacate; hydrocarbons such as liquid paraffin; ethoxylated stearyl alcohol, glycerol esters, isopropyl myristate, isotridecyl myristate, ethyl laureate, N-methylpyrrolidone, ethyl oleate, oleic acid, isopropyl adipate, isopropyl palmitate, octyl palmitate and 1,3-butanediol. Of the above, phthalates, isopropyl myristate, isotridecyl myristate and octyl palmitate are currently preferred. These substances can be used either alone or as a mixture or mixtures thereof.

Polyamines for use in the present invention should have two or more free amine groups to react with the ketone moiety of the adhesive. In the simplest embodiment, hydrazine, or hydrazine hydrate, may be used as the polyamine. However, we have established that it is highly preferable that the reactive amine should be bound directly to another nitrogen, or to another group providing the same or generally equivalent electronegativity as another nitrogen. Thus, dihydrazine compounds and linked amine compounds are particularly preferred. Examples of the latter include dialkyl triamines, especially diethylene triamine, but other suitable triamine and polyamine compounds will be readily apparent to those skilled in the art.

Dihydrazine compounds are especially preferably dihydrazides of polybasic organic acids, especially dicarboxylic acids. Examples of aromatic dicarboxylic acids include phthalic acid, isophthalic acid and terephthalic acid, although others will be readily apparent to those skilled in the art. Particularly preferred dihydrazides are those of aliphatic saturated dicarboxylic acids, especially those having 2–10 carbon atoms, and dihydrazides of oxalic acid and sebacic acids are suitable examples, while the dihydrazide of adipic acid is currently preferred (also known as adipic acid diamine and adipohydrazide). It will be apparent that polyhydrazides may also be employed.

We prefer that the polyamines be used in an amount generally between about 0.05% and 2% of the adhesive, more specifically between about 0.3% and 1%, although individual polyamines will have different optima for different adhesives. In addition, it will be appreciated that the quantity of the polyamine that is required may vary depending upon the amount of plasticiser that is used. We prefer that the amount of crosslinker that is added results in gelation of the adhesive, and is such that the adhesive cannot be subsequently dissolved by a solvent after crosslinking.

Polymers suitable for use as the hard portion of the block copolymer possess glass transition temperatures above room temperature. Suitable monomers for use in forming the hard segment polymer include styrene, α-methylstyrene, methyl methacrylate and vinyl pyrrolidone, although other suitable monomers will be readily apparent to those skilled in the art. Polystyrene and polymethyl methacrylate have been found to be suitable for the present invention.

It is preferred that the hard portion of the block copolymer forms from 3–30% w/w of the total block copolymer, particularly preferably from 5–15% w/w.

Particularly suitable block copolymers have soft portions which have been at least partially chemically cross-linked prior to cross-linking with polyamine. Such initial cross-linking may be effected by any suitable cross-linking agent. It is particularly preferable that the cross-linking agent be in the form of a monomer suitable for incorporation into the soft segment during polymerisation. Preferably the cross-linking agent has two, or more, radically polymerisable groups, such as a vinyl group, per molecule of the monomer, at least one tending to remain unchanged during the initial polymerisation, thereby to permit cross-linking of the resulting block copolymer.

Suitable initial cross-linking agents for use in the present invention include divinylbenzene, methylene bis-acrylamide, ethylene glycol di(meth)acrylate, ethylene glycol tetra(meth)acrylate, propylene glycol di(meth)acrylate, butylene glycol di(meth)acrylate, or trimethylolpropane tri (meth)acrylate, although other suitable cross-linking agents will be readily apparent to those skilled in the art. A preferred initial cross-linking agent is tetraethylene glycol dimethacrylate. It is preferred that the initial cross-linking agent comprises about 0.01–0.6% by weight of the block copolymer, with 0.1–0.4% by weight being particularly preferred.

Methods for the production of block copolymers from their monomeric constituents are well known. Block copolymer portions may be produced by any suitable method, such as step growth, anionic, cationic and free radical methods (Block Copolymers, supra). Free radical methods are generally preferred over other methods, such as anionic polymerisation, as the solvent and the monomer do not have to be purified.

Suitable initiators for polymerisation include polymeric peroxides with more than one peroxide moiety per molecule. One suitable initiator has been found to be 'Perhexa MC' (1,1'-di-tertbutyl-peroxy-2-methyl cyclohexane, Nihon Yusi C.C.). This compound contains two tertiary butyl peroxy groups which allow stepwise polymerisation of the hard and soft segments of the block copolymer. The initiator CH-50-AL (Peroxid-Chemie GmbH) has also been found to be suitable in the manufacture of compounds of the present invention. Choice of reaction conditions is well within the skill of one in the art, once a suitable initiator has been chosen.

The initiator is preferably used in an amount of 0.005–0.1% by weight of the block copolymer, with 0.01–0.05% by weight being particularly preferred, although it will be appreciated that the amount chosen is, again, well within the skill of one in the art. In particular, it is preferred that the amount should not be so much as to cause instant gelling of the mix, nor so low as to slow down polymerisation and to leave excess residual monomers. A preferred level of residual monomers is below 2000 ppm. It will also be appreciated that the amount of initiator will vary substantially, depending on such considerations as the initiator itself and the nature of the monomers.

It will be appreciated that there is no particular restriction on further substances being used in association with the adhesive of the invention. For example, suitable agents may be used to inhibit crystallisation of drug in the adhesive, where the adhesive is to be used in a patch, for instance. Many agents will be apparent to those skilled in the art, and polyethylene glycol is generally particularly effective. However, in general, it has been found that compounds to be delivered from patches of the invention are generally less likely to crystallise than they are in prior art systems.

Where the bioadhesive material of the present invention is to be used in association with a patch in order to hold a drug, then suitable drugs are biologically active compounds or mixtures of compounds that have therapeutic, prophylactic or other beneficial pharmacological or physiological effects.

Examples of drugs that may be used in combination with the bioadhesive material of the present invention include anti-arrhythmic drugs, anticoagulants, antidiabetics, antiepileptics, antifungals, antigout, antimalarials, antimuscarinic agents, antineoplasic agents, antiprotozoal agents, thyroid and antithyroid agents, anxiolytic sedatives and neuroleptics, beta blocking agents, drugs affecting bone metabolism, cardiac inotropic agents, chelating agents, antidotes and antagonists, corticosteroids, cough suppressants, expectorants and mucolytics, dermatological agents, diuretics, gastro-intestinal agents, general and local anaesthetics, histamine H1 and H2 receptor antagonists, nitrates, vitamins, opioid analgesics, parasympathomimetics, anti-asthma agents, muscle relaxants, stimulants and anorectics, sympathomimetics, thyroid agents, xanthines, lipid regulating agents, antiinflamatory drugs, analgesics, antiarthritic drugs, antispasmodics, antidepressants, antipsychotic drugs, tranquillisers, narcotic antagonists, antiparkinsonism agents, cholinergic agonists, anticancer drugs, immunosupressive agents, antiviral agents, antibiotic agents, appetite suppressants, antiemetics, anticholinergics, antihistamines, antimigraine agents, coronary, cerebral or peripheral vasodilators, hormonal agents, contraceptive agents, antithrombotic agents, diuretics, antihypertensive agents and cardiovascular drugs. Other drugs will be readily apparent to those skilled in the art.

Examples of specific drugs include steroids such as oestradiol, progesterone, norgestrel, levonorgestrel, norethisterone, modroxyprogestrone acetate, testosterone and their esters; nitro-compounds such as nitroglycerine and isosorbide nitrates; vitamins $D_2$ and $D_3$, nicotine, chlorpheniramine, terfenadine, triprobidine, hydrocortisone, oxicam derivatives such as piroxicam, ketoprofen, mucopolysaccharides such as thiomucase, buprenorphine, fentanyl, naloxone, codeine, dihydroergotamine, pizotiline, salbutamol, terbutaline, prostaglandins such as misoprostol and enprostil, omeprazole, imipramine, benzamides such as growth releasing factor and somatostatin, clonidine, dihydropyridines such as nifedipine, verapamil, ephidrine, pindolol, metoprolol, spironolactone, nicardipine hydrochloride, calcitriol, thiazides such as hydrochlorothiazide, flunarizine, sydononimides such as molsidomine, sulphated polysaccharides such as heparin fractions, as well as pharmaceutically acceptable equivalents thereof and pharmaceutically acceptable esters and the salts of such compounds with pharmaceutically acceptable acids and bases as appropriate. It will be appreciated that, while various drugs have been exemplified above, some drugs are more suitable for use in transdermal delivery systems than others. While a transdermal delivery system may deliver a quantity of a drug, this quantity may not be the optimum therapeutic dose. Essentially, any drug that can be delivered by a patch and which does not substantially crystallise at levels too low to be useful is envisaged as being useful in patches of the present invention.

It will be appreciated that, while various drugs have been exemplified above, some drugs are more suitable for use in transdermal delivery systems than others. While a transdermal delivery system may deliver a quantity of a drug, this quantity may not be the optimum therapeutic dose.

In general, the adhesive polymer may be prepared in any suitable manner as known in the art. This will generally comprise the adhesive being prepared in a solvent and, prior to removal of the solvent, it is preferable to involve, as a final step, the polyamine. This is mixed with the prepared adhesive solution and then applied to the tape or patch, or any other suitable application requiring such an adhesive material. A further advantage of the present invention is that the cross-linking time is generally substantially reduced, so that manufacture is easier. The solvent can be removed as known in the art.

The preferred adhesive strength of the bioadhesive material is such that, when applied to a tape or patch, the tape or patch can be applied to the skin and then removed without removing the stratum corneum layer of the skin surface. In particular, an adhesive strength of about 30 g/inch (~1.2 g/mm) to about 300 g/inch (~12 g/mm), more preferably about 40 g/inch (~1.6 g/mm) to about 200 g/inch (~8 g/mm), is preferred for the bioadhesive, although the skilled person will recognise appropriate strengths. Materials with adhesive strength greater than about 300 g/inch (~8 g/mm) are likely to cause skin irritation when the tape is removed, as the outer skin layer is concomitantly removed.

It will be appreciated that the present invention further provides a process for the manufacture of adhesive materials as described herein, comprising preparing an adhesive material comprising substantially non-enolisable ketone groups, blending said material with a suitable plasticiser therefor and, at the same time, or thereafter, further blending therewith a polyamine cross-linking agent and allowing the mixture to complete the cross-linking reaction. The adhesive material will normally be prepared in solution, prior to the addition of plasticiser and polyamine. Cross-linking will normally be done under conditions of heat.

The present invention will now be illustrated further with reference to the following, non-binding Examples and Comparative Examples.

EXAMPLE 1

Preparation of Block Copolymeric Adhesives

The adhesive compound used in the following Examples was prepared in a "2-1" synthesis. The first step effectively provides the soft segment of the block copolymer, while the second step completes formation of the block copolymer. In the third step, cross-linking occurs, to form an insoluble product. Thus, this step is largely for illustration, as it must be performed in situ. In general, the following Examples start with the product of step 2. Some also use only the product of step 1, and modifications to either step are noted, as appropriate.

Step 1:

115 g of 2-ethylhexyl acrylate, 84 g of diacetone acrylamide, 115 g of butyl acrylate and 0.72 g tetramethylene glycol dimethacrylate were mixed, in order to obtain a homogeneous solution. The solution was placed in a flask, and 200 ml of ethyl acetate along with 200 ml of toluene were added. The solution was heated to 80° C. under nitrogen, then 0.05 g of 1,1'-di-tert-butylperoxy-2-methyl cyclohexane dissolved in 10 ml of ethyl acetate were added. Polymerisation was allowed to proceed for 24 hours at this temperature. This step produced the soft segments.

Step 2:

After 24 hours, 45 g methyl methacrylate and 300 ml of toluene were added to the mix of Step 1. The solution was then heated to 99° C. in order to initiate the second stage polymerisation step, which was continued for 12 hours at 99° C.

After this time, the polymer was transferred to a bottle for cooling. The resulting solution contains the pre-crosslinked polymer, and can be stored for substantial periods. The average molecular weight of the polymer produced in this way was estimated to be 358,000 Da by gel permeation chromatography. This solution can be used, per se, but the solids content of the solution generally varies between about 30 and 50%. Accordingly, it is preferred to dry the solution, with heating, in order to obtain a first stage adhesive. This adhesive generally corresponds to that of WO 99/02141, and, after the evaporation stage, already possesses a degree of cross-linking between the soft segments of the block copolymer. This adhesive is then dissolved at a rate of 1.0 g per 2.0 g of a 2:5 v/v mixture of ethyl acetate and toluene. This resulting solution was then used in the following Examples, unless otherwise specified.

Step 3:

3.0 g of the solution of step 2 (containing 1.0 g of solid adhesive) were mixed with plasticiser, as specified [e.g. isopropyl myristate (IPM), 1.0 g], and cross-linker [1.0 ml of a solution of adipic acid diamine in 3:1 v/v methanol/water (0.5 g in 100 ml), unless otherwise specified] was mixed and coated onto substrate, generally a PET (polyethylene terephthalate) film measuring 20×20 cm. This was then heated at 80° C. for 20 minutes, covered with a PET release liner, and then allowed to stand at 40° C. for 24 hours to complete cross-linking. The 20×20 PET film is then typically cut into strips measuring 10×2.5 cm.

The PET strip is generally subjected to the following test:

Bakelite 180° Peel strength test

Peel strength was measured by coating each sample onto a PET strip 25 mm wide and 100 mm long and applying the strip to a bakelite plate. Then, a roller having a load of 300 g is rolled back and forth thereon to secure the sample to the plate. The sample is subsequently peeled off at an angle of 180° at a rate of 300 mm/min. to determine peel force. Unless otherwise specified, peel force is measured herein by this test.

EXAMPLE 2

1) Molecular weight and molecular weight distribution

Tables 1 and 1a summarise the polymerisation conditions and other properties (molecular weight, and cohesion) for a range of block copolymer adhesives subsequently used to form adhesives of the invention.

Numerical values for monomers and catalyst in the table are grams.

Numerical values for solvents are ml.

The molecular weights are calibrated as for polystyrene.

The Mw of EBDMX-2 was not obtainable because of gel formation, suggesting its Mw is far greater than that of EBDMX-3.

EBDMX-2 was further used and characterised.

EXAMPLE 3

Nitroglycerine Patch

One desirable type of patch is a nitroglycerine patch. High amounts of nitroglycerine in the patch is important. Nitroglycerine is a liquid and makes the adhesive softer, so that cross-linking is necessary. Accordingly, the following experiment was performed to establish whether a nitroglycerine patch could be made in accordance with the present invention.

The main problem concerns the possibility of cross-linking nitroglycerine and concomitant decomposition in the

TABLE 1

|  | EDMX-1 | EDMX-2 | EBDMX-1 | EBDMX-2 | EBDMX-3 | EBDMX-4 |
|---|---|---|---|---|---|---|
| First Step |  |  |  |  |  |  |
| EHA | 129 | 258 | 115 | 115 | 115 | 115 |
| DA | 21 | 42 | 84 | 84 | 84 | 84 |
| BA |  |  | 115 | 115 | 115 | 115 |
| EA |  |  |  |  |  | 63 |
| 4EG | 0.12 | 0.48 | 0.72 | 0.72 | 0.5 | 0.35 |
| Cat | 0.1 | 0.033 | 0.075 | 0.05 | 0.05 | 0.05 |
| EthyAc | 300 | 350 | 200 | 300 | 400 | 300 |
| Toluene |  |  | 200 | 100 | 100 | 100 |
| Second Step |  |  |  |  |  |  |
| MMA | 15 | 30 | 45 | 45 | 45 | 45 |
| Toluene | 200 | 200 |  | 100 | 300 | 300 |
| Results |  |  |  |  |  |  |
| Solid % | 35 | 46 |  | 39 |  |  |
| Cohesion | Weak | Fair | Fair | Excellent | Good | Weak |

The molecular weights of some of the above adhesive polymers were calibrated against polystyrene using gel permeation chromatography. The results are shown in Table 1a, below.

TABLE 1a

| Code Name | EDX-1 | EDX-2 | EBDX-1 | EBDX-2 | EBDX-3 |
|---|---|---|---|---|---|
| Molecular Weight | 112,000 | 155,000 | 199,000 | 335,000 | 311,000 |

| Code Name | EDMX-1 | EDMX-2 | EB-DMX-1 | EB-DMX-2 | EB-DMX-3 |
|---|---|---|---|---|---|
| Mw. | 161,000 | 233,000 | 262,000 | >>400,000 | 358,000 |

EHA: 2-ethylhexyl acrylate
DA: Diacetone acrylamide
BA: Butyl acrylate
EA: Ethyl acrylate
4EG: Tetraethyleneglycol dimethacrylate
Cat: Catalyst (Perhexa MC, Nihon Oil and Fat Co.)
EthyAc: Ethylacetate
MMA: Methylmethacrylate adhesive. Thus, the stability of the nitroester bond was checked, during the cross-linking process.

Nitroglycerine was unavailable, so 5-isosorbide mononitrate (5-ISMN) was used instead. Both nitroglycerine and 5-ISMN have a nitroester group in common. If 5-ISMN is stable during the cross-linking process, then so should nitroglycerine be.

a) Preparation of sample patch

TABLE 2

|  | Sample 1 | Sample 2 |
|---|---|---|
| Adhesive* (g) | 1.0 | 1.0 |
| 5-ISMN (g) | 0.1 | 0.1 |
| GML (g) | 0.05 | 0.05 |
| IPM (g) | 0.8 | 0.8 |
| Diethylene Triamine (g) | 0 | 0.02 |

*Product of Example 1, step 2
GML-glycerine monolaurate, a permeation enhancer
Heated at –80° C., 15 minutes.

b) ISMN determination

The ISMN-containing patches were subjected to ethanol extraction for 24 hours at 36° C.

HPLC

Column: ODS (octadecyl silane) type

Column temperature: 40° C.

Eluent: Mixture of 500 ml of water containing 1.5 g of ammonium acetate and 1.0 g of acetic acid and 200 ml of methanol.

Detection wavelength: 250 nm

The peak height of ISMN corrected by the medicated adhesive weight was:

For Sample 1: 0.076, and 0.080

For Sample 2: 0.073, and 0.080

Thus, it would appear that no decomposition occurs during the cross-linking process, and that the adhesive of the present invention could suitably be employed in the preparation of a nitroglycerine transdermal patch.

EXAMPLE 4

Useable Plasticisers

Using 0.6 g of plasticiser, but otherwise following Example 1, steps 1 to 3, PET films were prepared (10×2.5 cm). The following plasticisers were tested: (1) isopropyl palmitate, (2) methyl oleate, and (3) olive oil.

Each of the cross-linked adhesives containing plasticisers (1) and (2) performed well to yield useful adhesive. Olive oil, however, bled out of adhesive (3) to the surface and the film had no adhesive property.

Thus, provided that the oily component has a certain degree of compatibility with the adhesive, then it can be used as a softening agent, or plasticiser.

EXAMPLE 5

Amount of Softening Agent

PET films were prepared as in Example 1, but using either isopropyl myristate (IPM) or methyl oleate (MO) in varying amounts, as set out below.

TABLE 3

| IPM | |
|---|---|
| Amount of IPM (g) | Property |
| 0.05, 0.1, | Hard and sticky. Paper removal. |
| 0.2, 0.4 | Hard and sticky. No paper removal. |
| 0.6 to 1.6 | Soft and mild feeling. Smooth removal. No paper removal. |
| 2.0 | Very soft. No paper removal. Can be used. |
| 3.0 | Very weak cohesion. Cannot be used. |

"Paper removal" means that when the tape is removed from paper having a rough surface, such as newspaper, then after one or more applications, some cellulose fibre is removed together with the tape.

TABLE 4

| MO | |
|---|---|
| Amount of MO (g) | Property |
| 0.05, 0.1, | Hard and sticky. Paper removal. |
| 0.2, 0.4 | Hard and sticky. No paper removal. |
| 0.6 to 1.6 | Soft and mild feeling. Smooth removal. |

TABLE 4-continued

| MO | |
|---|---|
| Amount of MO (g) | Property |
| 2.0, 3.0 | No paper removal. Very weak cohesion. Cannot be used. |

EXAMPLE 6

Amount of Cross-linking Agent

PET films were prepared in accordance with Example 1, but using varying amounts of the adipic acid diamine in methanol and water, as follows; 0.1, 0.2, 0.3, 0.6, 1.0, 1.6, 2.0, 4.0, and 7.0 ml.

The effect on physical properties of adhesive is as shown in Table 5 below.

TABLE 5

| Amount of adipic acid Diamine solution (ml) | Property |
|---|---|
| 0.1 to 0.3 | Soft and sticky. At removal, part of adhesive remains on paper |
| 0.6 to 2.0 | Soft and mild feeling. Smooth removal. No paper removal. |
| 4.0 to 7.0 | Too much cross-linking and no adhesion. Cannot be used. |

EXAMPLE 7

Water Vapour Permeability

High water vapour permeability (wvp) usually means high breathability for skin, important to reduce skin irritation, especially for long term application of tape to skin.

Two sample tapes, prepared with different amounts of plasticiser, were used for determination of wvp. A commercial acrylic adhesive from National Starch was also used as a reference sample.

The results are set out in Table 6, below. PET strips were prepared in accordance with Example 1.

TABLE 6

| | *Sample Compositions | | |
|---|---|---|---|
| | Sample 1 | Sample 2 | Sample 3 |
| Adhesive (g) | 1.0 | 1.0 1.2 | 0 0 |
| Adipic acid diamine (ml) | 1.0 | 1.0 | 0 |
| National Starch Adhesive (g)[1] | 0 | 0 | 1.0 |

[1]Grade No. 387-2287
*Preparation of mixture solution for Sample 1 and 2

The adhesive prepared in accordance with step 2 was dissolved to 30% by weight in the mixture of ethyl acetate and toluene.

*Preparation of test adhesive films

The solutions of samples 1, 2 and 3 were coated onto a PET release liner and dried for 15 minutes at 80° C. The films were transferred to filter paper with the aid of a press roller. The paper base adhesive films were then subjected to a wvp test. Paper was selected as the backing film because of its high water permeability, in order not to interfere with the results.

*Vapour permeability measurement:

100 ml beakers containing 30 ml water were covered with the Sample films. These were allowed to stand in a 40° C. oven for 24 hours. Weight loss over 24 hours was determined for each beaker, and these values were converted into the value of water permeability of the adhesives.

The vapour permeability values are shown in table 7 below. The units are mg/cm$^2$×24 hours.

TABLE 7

| | Adhesive thickness (µ) | Water loss (g) | Wvp (mg/cm$^2$ day) | Wvp of 6 um (calculated) (mg/cm$^2$ day) |
|---|---|---|---|---|
| National Starch | 65 | 1.3 | 45.8 | 49.8 |
| adhesive | 79 | 1.04 | 36.7 | 48.4 |
| Adhesive | 73 | 2.63 | 92.9 | 113 |
| (1.2 g IPM) | 66 | 2.98 | 105 | 116 |
| Adhesive | 54 | 2.98 | 105 | 95.1 |
| (0.6 g IPM) | 58 | 3.01 | 106 | 102 |
| Uncoated filter paper* | 143 | 13.24 | 467 | |

*The thickness of the paper is a constant and is not included in the preceding figures of this column.

It is clearly shown that the vapour permeability of the cross-linked adhesive is far greater than that of the commercial acrylic adhesive. It is also notable the cross-linked adhesive with the greater amount of IPM has better vapour permeability than that with less.

EXAMPLE 8

Stability of Drug-containing Patches

Active and non-active ingredients for the four formulations are shown in Table 8 below.

TABLE 8

| Ingredient | Px-No-Cr | Px-Cr | Vit-No-Cr | Vit-Cr |
|---|---|---|---|---|
| Adhesive (g) | 0.5 | 0.5 | 0.5 | 0.5 |
| IPM (G) | 0.5 | 0.5 | 0.5 | 0.5 |
| Adipic acid diamine (mg) | 0 | 1.5 | 0 | 1.5 |
| Piroxicam (mg) | 45 | 45 | | |
| Vitamin D$_2$ (mg) | | | 100 | 100 |
| BHT (mg) | | | 2.5 | 2.5 |

BHT - butyl hydroxytoluene, an antioxidant

The mixed solutions were coated onto PET film and heated at 80° C. for 20 minutes. The content of drug was determined both immediately after preparation and after storage at 6 days at 60° C.

The cross-linked medicated patches, Px-Cr, and Vit-Cr, were prepared with no problem. They feel soft and are gentle on the skin. Those without the plasticiser were uncomfortable, hard and sticky.

The content of vitamin D$_2$ and Piroxicam in the patches, at both measured times, was established to be slightly more than 90% of the theoretical possible total after initial preparation, and that there was no measurable deterioration after 6 days.

COMPARATIVE EXAMPLES

Nitto U.S. Pat. No. 5,298,258 discloses an acrylic adhesive, comprising an acryl ester and an acrylic acid copolymer, the adhesive being mixed with 80–100% IPM and cross-linked with aluminium triacetylacetonate and irradiation.

The composition of adhesive we selected from the patent is:

| 2-ethylhexyl acrylate | 238 g |
|---|---|
| Acrylic acid | 12.5 g |
| Ethyl acetate (Solvent) | 150 g |
| AIBN (Initiator) | 0.1 g |

AIBN -azo-bis-isobutylnitrile.

Herein, this adhesive is referred to as Nitto Adhesive.

Comparative Example 1

Comparison with Nitto Adhesive
Optimisation of cross-linking agent for the both adhesives In this Example, PET strips were 20 mm in width. In the adhesive of Example 1, adipic acid diamine was dissolved in methanol+water (19:1 by volume) to a concentration of 0.5%.

The Nitto Adhesive was dissolved in ethyl acetate. The cross-linking agent (aluminium tri-acetylacetonate) was dissolved in acetylacetone+ethylacetate (1:1 by volume) solution to a concentration of 0.5%.

IPM was used as plasticiser for both. Heating was at 80° C. for 20 minutes in both cases.

Table 8 and 9 show the results.

TABLE 9

Adhesive of the Invention

| Condition | 1 | 2 | 3 | 4 | 5 |
|---|---|---|---|---|---|
| Amount of adhesive (g) | 1.0 | 1.0 | 1.0 | 1.0 | 1.0 |
| Amount of IPM (g) | 1.0 | 1.0 | 1.0 | 1.0 | 1.0 |
| Amount of cross-linker (mg) | 0 | 1.5 | 3.0 | 6.0 | 12.0 |
| Adhesion strength (g/20 mm) | ≦5 | 50 | 45 | 25 | 20 |
| Special comment | Cohesive failure | Partial cohesive failure | | | |

TABLE 10

Nitto Adhesive

| Condition | 1 | 2 | 3 | 4 |
|---|---|---|---|---|
| Amount of adhesive (g) | 1.0 | 1.0 | 1.0 | 1.0 |
| Amount of IPM (g) | 1.0 | 1.0 | 1.0 | 1.0 |
| Amount of cross-linker (mg) | 0 | 5.0 | 10 | 20 |
| Adhesion strength (g/20 mm) | ≦5 | 110 | 50 | 10 |
| Special comment | Cohesive failure | Partial cohesive failure | | |

From the results, it can be seen that the best formulation for the adhesive of the invention and Nitto adhesive was Condition 3 for the both.

Comparative Example 2

Time Required for Cross-Linking of Adhesives

Time required for cross-linking of adhesive is not so important for plain non-medicated tape, but is vital for medicated patch manufacture. However, from the drug-stability viewpoint, the shorter the heating time the better and the lower the heating temperature the better. Heating time for both cross-linked adhesives (Nitto and adhesive of invention) was established at the relatively low temperature of 60° C.

Using the most suitable amount of cross-linker for both adhesives, the necessary time for cross-linking for the Nitto Adhesive was 20 minutes, compared to 10, for the adhesive of the invention, which is advantageous for a medicated patch.

Comparative Example 3

Saturation Concentration of Drugs

Oestradiol (a hydrophobic drug) and piroxicam (a hydrophilic drug), were investigated to establish their saturation concentrations in the two adhesives. As before, formulations 3 in each of Tables 9 and 10 were used. The results are summarised in Tables 11 and 12.

TABLE 11

Adhesive of invention

| Condition | 1 | 2 | 3 | 4 |
|---|---|---|---|---|
| Amount of adhesive (g) | 1.0 | 1.0 | 1.0 | 1.0 |
| Amount of IPM (g) | 1.0 | 1.0 | 1.0 | 1.0 |
| Amount of cross-linker (mg) | 3.0 | 3.0 | 3.0 | 3.0 |
| Amount of oestradiol (mg) | 50 | 100 | 120 | 150 |
| Crystallisation |  |  | ¦ | ¦ |
| Amount of piroxicam | 30 | 40 | 50 | 75 |
| Crystallisation |  |  | ¦ | ¦ |

No crystallisation. Drug is dissolved
¦ Crystallisation

TABLE 12

Nitto Adhesive

| Condition | 1 | 2 | 3 | 4 |
|---|---|---|---|---|
| Amount of adhesive (g) | 1.0 | 1.0 | 1.0 | 1.0 |
| Amount of IPM (g) | 1.0 | 1.0 | 1.0 | 1.0 |
| Amount of cross-linker (mg) | 10 | 10 | 10 | 10 |
| Amount of oestradiol (mg) | 30 | 40 | 50 | 75 |
| Crystallisation |  | ¦ | ¦ | ¦ |
| Amount of piroxicam | 30 | 40 | 50 | 75 |
| Crystallisation |  | ¦ | ¦ | ¦ |

There is a clear advantage for the adhesive of the invention in both cases, but it is clear that the adhesive of the invention can hold three times more oestradiol than the Nitto adhesive.

Comparative Example 4

Necessary Amount of Cross-Linking Agent for Nitto Piroxicam Containing Patch

In Comparative Example 3, the piroxicam patch did not cross-link when the optimum cross-linking condition 4 was applied, while the oestradiol patch did cross-link. There was no problem with the adhesive of the invention.

It was decided to find out how much cross-linker was required for the Nitto piroxicam patch.

Table 13 shows the result of the experiment to find the minimum amount of cross-linker.

TABLE 13

Adhesion test result from Nitto Adhesive containing piroxicam

| Condition | 1 | 2 | 3 |
|---|---|---|---|
| Amount of adhesive (g) | 1.0 | 1.0 | 1.0 |
| Amount of IPM (g) | 1.0 | 1.0 | 1.0 |
| Amount of cross-linker (mg) | 10 | 20 | 40 |
| Piroxicam (mg) | 30 | 30 | 30 |
| Adhesion strength (g/20 mm) | $\leq 5$ | $\leq 5$ | 45 |
| Special comment | Cohesive failure | Cohesive failure |  |

From the table, it is obvious that the amount of cross-linker necessary for adequate cross-linking to Nitto Adhesive containing piroxicam is four times greater than plain Nitto Adhesive.

As piroxicam is weakly basic, it has an affinity for carboxylic acid (acrylic acid in the adhesive). When the piroxicam in the adhesive system reacts with acrylic acid, this reaction is in competition with the reaction of the Al cation with acrylic acid. This latter reaction is the cross-linking reaction. Logically, therefore, in the presence of piroxicam, the amount of cross-linker (Al compound) must be that must greater to enable cross-linking.

Comparative Example 5

Stability of Drugs in Nitto Adhesive

In Example 8, the stability of both vitamin $D_2$ and piroxicam is demonstrated for an adhesive of the invention. Similar experiments were performed on the Nitto adhesive.

The active and non-active ingredients for the four formulations are shown in Table 14.

TABLE 14

| Ingredient | Px-No-Cr | Px-Cr | Vit-No-Cr | Vit-Cr |
|---|---|---|---|---|
| Nitto Adhesive (g) | 1.0 | 1.0 | 1.0 | 1.0 |
| IPM (g) | 1.0 | 1.0 | 1.0 | 1.0 |
| Al triacetylacetonate (mg) | 0 | 40 | 0 | 40 |
| Piroxicam (mg) | 90 | 60 |  |  |
| Vitamin $D_2$ (mg) |  |  | 200 | 200 |
| BHT (mg) |  |  | 5.0 | 5.0 |

The mixed solutions were coated onto PET film and heated at 80° C. for 20 minutes. The content of drug was determined immediately after preparation and after storage for 6 days at 60° C.

While Piroxicam is stable both during the preparation process and after heating 60° C. for 6 days, vitamin $D_2$ is not only decomposed by ca. 30% during the preparation process, but is also decomposed a further 20% during the 6 day storage period in the Nitto adhesive lacking plasticiser.

Comparative Example 6

Antimicrobial Activity

The antimicrobial efficacy of an adhesive as prepared in Example 1 was compared with a commercially available substance.

The following products were evaluated:
Adhesive Tape of Example 1
  Active Compound
  None (Control)
  Chlorhexidine acetate
  0.5% w/w
  Chlorhexidine acetate
  1.0% w/w
Bactigras® Antiseptic Tulle Gras Dressing

| Active Compound | Manufacturer/Supplier | Lot Number |
| --- | --- | --- |
| Chlorhexidine acetate 0.5% | Smith & Nephew Medical Limited PO Box 81 Hessle Road HULL HU3 2 BN | 983308303 |

All samples were stored at room temperature.
Culture Media
  The following bacteriological culture media were used:

| | |
| --- | --- |
| Nutrient Agar (LabM; LAB 8) | NA |
| Mueller Hinton Agar (Oxoid; ml 37) | MHA |
| Tryptone Soy Broth, USP (LabM; LAB 4) | TSB |
| Maximum Recovery Diluent (DWS; G50011) | MRD |

All media were prepared in accordance with manufacturers' instructions and Standard Microbiology Method SMM/DSW0020/09.
Bacterial Strains
  The following organisms were used to assess antibacterial activity of the test products:

| Species | Type Culture Code | DWS Culture Code |
| --- | --- | --- |
| Escherichia coli | ATML 25922 | DWC 2415 |
| Pseudomonas aeruginosa | ATML 9027 | DWC 1766 |
| Staphylococcus aureus | ATML 6538 | DWC 1764 |

All organisms had been lodged previously in the DWS culture collection and were stored at −80±10° C. when not in use.
Procedure:
Preparation of Bacterial Inocula
  Each bacterial strain listed above was sub-cultured from frozen stock onto a sterile NA plate and incubated at 37±1° C. for 24±6 hours.
  After careful inspection of each incubated plate to confirm the presence of a pure culture, 4 or 5 isolated colonies were touched with a sterile bacteriological loop and sub-cultured into a sterile 20 ml aliquot of TSB. TSB was incubated at 37±1° C. for 24±6 hours to produce a dense broth culture.
  Each broth culture was used to produce a standardised bacterial suspension with turbidity equivalent to that of a 0.5 McFarland standard. This was achieved by dropwise addition of the broth to a sterile 9 ml aliquot of MRD until the required turbidity was obtained.
Preparation of Agar Plates
  For each combination of test product and bacterial culture, 3 sterile MHA plates were prepared, each being poured to a uniform depth of approximately 4 mm in a 90 mm petri dish. For each day of experimental work, additional MHA plates were prepared for use as sterility controls.

Determination of Antibacterial Activity
  Each standardised bacterial suspension was used to inoculate the surface of 3 MHA plates per test product by wetting a sterile swab in the suspension and streaking over the entire agar surface. This was repeated twice, rotating the plate each time to ensure even coverage. Plates were allowed to dry before continuing.
  A sterile cork borer was used to cut 9×20 mm discs from each test product. When moving between products the tool was dipped in ethanol and passed through a flame to decontaminate.
  For each combination of test product and organism, triplicate test plates were prepared. Each 20 mm disc was placed in the centre of an appropriately inoculated plate, ensuring intimate contact with the agar.
  After pressing down each disc once more, all plates were incubated at 37±1° C. for 24±2 hours. A sterile control plate was included with each batch.
  Each incubated plate was carefully examined for the presence of a clear zone around the disc, where bacterial growth was inhibited. If such a zone was present, its diameter was measured using calibrated electronic callipers. The diameter of the disc was included in the total zone diameter.

TABLE 15

Results for the test tape of Example 1 and for Bactigras ® Product as Determined using Disk Susceptibility Technique.

| Sample Code and Description | Test Organism | Diameter of Inhibition Zone (mm) | |
| --- | --- | --- | --- |
| | | Replicates | Mean |
| 032/99/001 Test Tape Control | Escherichia coli ATML 25922 | 24.74* 25.64* 24.25* | 24.9 |
| | Pseudomonas aeruginosa ATML 9027 | No Inhibition No Inhibition No Inhibition | No inhibition |
| | Staphylococcus aureus ATML 6538 | 26.48 25.60 24.70 | 25.6 |
| 032/99/002: Test Tape Chlorhexidine acetate 0.5% | Escherichia coli ATML 25922 | 33.94 33.32 33.47 | 33.6 |
| | Pseudomonas aeruginosa ATML 9027 | 28.06 28.28 30.11 | 28.8 |
| | Staphylococcus aureus ATML 6538 | 37.77 37.60 37.96 | 37.8 |
| 032/99/003 Test Tape Chlorhexidine acetate 1.0% | Escherichia coli ATML 25922 | 34.76 35.05 35.89 | 35.2 |
| | Pseudomonas aeruginosa ATML 9027 | 31.63 31.20 31.71 | 31.5 |
| | Staphylococcus aureus ATML 6538 | 37.90 38.63 38.73 | 38.4 |
| 032/99/004 Bactigras ® Chlorhexidine acetate 0.5% | Escherichia coli ATML 25922 | 23.00 24.05 24.59 | 23.9 |
| | Pseudomonas aeruginosa ATML 9027 | No Inhibition No Inhibition No Inhibition | No Inhibition |
| | Staphylococcus aureus ATML 6538 | 25.40 24.64 25.30 | 25.1 |

*Irregular zone: diameter stated is maximum observed.

Thus, it can be seen that not only do the adhesives of the invention seem to display antimicrobial activity even without active ingredient, but that they serve to deliver the active ingredient more effectively than the Bactigras product, as evidenced by the greater zones of inhibition. The efficiency is such that *P. aeruginosa* can be affected by a tape of the invention carrying chlorhexidine acetate, where Bactigras cannot.

EXAMPLE 9

Polymer made with Allyl Acetoacetate

1. Polymer synthesis

The adhesive compound was made in a one step synthesis.

100 g of 2-ethylhexyl acrylate, 100 g of butyl acrylate, and 55 g of allyl acetoacetate were mixed, in order to obtain a homogeneous solution. The solution was placed in a flask, and 250 ml ethyl acetate were added. The solution was heated to 65° C. under nitrogen, then 0.04 g of CCC"-azobisisobutyronitrile, dissolved in 10 cm$^3$ of ethyl acetate, were added. Polymerisation was allowed to proceed for 24 hrs.

After that, the polymer was transferred to a bottle for cooling. Ethyl acetate was added to the polymer solution to obtain a 33.3% polymer solution. The resulting polymer solution was dried in accordance with step 2 of Example 1. The average molecular weight of the polymer produced in this way was estimated to be 635,000 Da by gel permeation chromatography.

2. Crosslinking reaction

A mixture of a polymer solution thus obtained and prepared in accordance with step 3 of Example 1, 0.8 g of plasticiser, and adipic acid diamine in methanol (0.5 g in 100 cc) of 0.6 cc was mixed and coated onto a PET film. This was heated at 80° C. for 20 minutes, followed by standing at 60° C. for 24 hrs to complete the crosslinking reaction. The plasticisers chosen were isopropyl myristate and methyl oleate.

3. Physical properties of oil gel adhesives

The physical properties of the two adhesives were measured. The result are shown in Table 16, below.

TABLE 16

| Oily substance | Properties | Thickness (um) | Adhesion strength (g/20 mm) |
| --- | --- | --- | --- |
| Isopropyl myristate | Soft and mild feeling. Smooth removal. No paper removal. | 90 | 80 |
| Methyl oleate | Soft and mild feeling. Smooth removal. No paper removal | 85 | 95 |

EXAMPLE 10

Preferred Pre-Crosslinked Adhesive

Scale Up

The following is how the initial, pre-crosslinked adhesive is scaled up, for economic production.

Reactor. 300 liter inner volume, that has a heating system that can heat up to 120° C.

A reflux condenser system, and a temperature control system of ±2° C.

First step of polymerisation (85° C., 6 hours)

Feed monomers solvents and initiator are described below:

| | (kg) | |
| --- | --- | --- |
| BA | (butyl acrylate) | 23.2 |

-continued

| 2 EHA | (2-ethylhexyl acrylate) | 22.6 |
| --- | --- | --- |
| DAAM | (diacetone acrylamide) | 15.6 |
| VAc | (vinyl acetate) | 3.0 |
| TEGDMA | (tetraethylene glycol dimethacrylate) | 0.12 |
| Perhexa MC | | 0.12 |
| Ethylacetate | | 44 |
| Toluene | | 22.4 |

Second step (105° C. 6 hours)

After the first step, 9.2 kg MMA and 40 kg of toluene are added to the mix and polymerisation is continued.

After the two steps of polymerisation, the initiator is almost completely consumed and has become part of the polymer produced. Based upon the decomposition data and reaction conditions, the residual amount of initiator is calculated to be less than 10 ppm.

EXAMPLE 11

Alternative Compositions

Monomer composition and reaction conditions.

The monomer composition of three further adhesive polymers are shown in Table 17 below. The figure shows weight (g).

TABLE 17

| Monomer | A | B | C |
| --- | --- | --- | --- |
| BA | 23.2 | 23.2 | 23.2 |
| 2 EHA | 22.6 | 22.6 | 22.6 |
| DAAM | 15.6 | 10 | 5 |
| TEGDMA | 0.12 | 0.12 | 0.12 |
| Vac | 3 | 3 | 3 |
| MMA | 9.2 | 9.2 | 9.2 |

The solvent was a mixture of ethylacetate and toluene (60+20) (g). The initiator was 0.01 g of Perhexa MC. The reaction temperature was 90° C. The reaction time was 15 hours.

EXAMPLE 12

Cross-Linking Reaction and Physical Properties

Cross-linking reaction

The adhesive of Example 9 were used to prepare adhesive polymer solutions in a manner similar to that of Example 1, but using 0.8 g IPM or methyl oleate, and 0.6 ml adipic acid diamine in methanol-water (0.5 g in 100 ml [methanol 70 and water 30]). The solutions were mixed and coated onto PET film which was then heated at 80° C. for 20 minutes, followed by standing at 60° C. for 24 hours to complete cross-linking.

As a reference, the cross-linked samples without plasticiser were also prepared and their physical properties were measured.

Physical properties

Each sample was subjected to the bakelite peel strength test.

Paper application and removal test method

The sample strip is applied to a news paper. Then, a roller of a load of 300 g is moved back and forth thereover to secure the strip to the paper. Subsequently, the sample was peeled off, and (1) the presence of residual adhesive on the paper, and (2) the adhesive's paper removal were observed.

The results are shown in Tables 18 to 23, below.

TABLE 18

Polymer (EDX-1)

| Plasticiser | Properties | Thickness of adhesive (um) | Adhesion strength (g/25 mm) |
|---|---|---|---|
| Isopropyl myristate | (Soft and mild feeling) No residual adhesive when removed No paper removal | 90 | 50 |
| Methyl oleate | (Soft and mild feeling) No residual adhesive when removed No paper removal | 85 | 55 |
| None | (Hard feeling) No residual adhesive when removed Paper removal | 80 | 750 |

TABLE 19

Polymer (EDMX-1)

| Plasticiser | Properties | Thickness of adhesive (um) | Adhesion strength (g/25 mm) |
|---|---|---|---|
| Isopropyl myristate | (Soft and mild feeling) No residual adhesive when removed No paper removal | 95 | 60 |
| Methyl oleate | (Soft and mild feeling) No residual adhesive when removed No paper removal | 85 | 60 |
| None | (Hard feeling) No residual adhesive when removed Paper removal | 85 | 1,150 |

TABLE 20

Polymer (EBDX-1)

| Plasticiser | Properties | Thickness of adhesive (um) | Adhesion strength (g/25 mm) |
|---|---|---|---|
| Isopropyl myristate | (Soft and mild feeling) No residual adhesive when removed No paper removal | 70 | 65 |
| Methyl oleate | (Soft and mild feeling) No residual adhesive when removed No paper removal | 85 | 75 |
| None | (Hard feeling) No residual adhesive when removed Paper removal | 90 | 850 |

TABLE 21

Polymer (EBDMX-1)

| Plasticiser | Properties | Thickness of adhesive (um) | Adhesion strength (g/25 mm) |
|---|---|---|---|
| Isopropyl myristate | (Soft and mild feeling) No residual adhesive when removed No paper removal | 100 | 70 |
| Methyl oleate | (Soft and mild feeling) No residual adhesive when removed No paper removal | 90 | 70 |
| None | (Hard feeling) No residual adhesive when removed Paper removal | 85 | 1,250 |

TABLE 22

Polymer (EBDX-2)

| Plasticiser | Properties | Thickness of adhesive (um) | Adhesion strength (g/25 mm) |
|---|---|---|---|
| Isopropyl myristate | (Soft and mild feeling) No residual adhesive when removed No paper removal | 80 | 60 |
| Methyl oleate | (Soft and mild feeling) No residual adhesive when removed No paper removal | 80 | 75 |
| None | (Hard feeling) No residual adhesive when removed Paper removal | 85 | 1,350 |

TABLE 23

Polymer (EBDMX-2)

| Plasticiser | Properties | Thickness of adhesive (um) | Adhesion strength (g/25 mm) |
|---|---|---|---|
| Isopropyl myristate | (Soft and mild feeling) No residual adhesive when removed No paper removal | 85 | 75 |
| Methyl oleate | (Soft and mild feeling) No residual adhesive when removed No paper removal | 100 | 75 |
| None | (Hard feeling) No residual adhesive when removed Paper removal | 80 | 1,450 |

EXAMPLE 13

Varying Peel Strength by Varying Amount of Plasticiser (1) Change of amount of plasticiser The adhesive was prepared in accordance with Example 1. The amount of plasticiser was as shown in Table 24 below. In all, two lots of each of seven different adhesives were prepared.

TABLE 24

| Adhesive Lot | 1 | 2 | 3 | 4 | 5 | 6 | 7 |
|---|---|---|---|---|---|---|---|
| Adhesive (g) | 1.0 | 1.0 | 1.0 | 1.0 | 1.0 | 1.0 | 1.0 |
| Isopropyl Myristate (g) | 1.2 | 0.8 | 0.6 | 0.4 | 0.2 | 0.1 | 0 |
| Cross-linker (mg) | 5 | 5 | 5 | 5 | 5 | 5 | 5 |
| Peel Strength (kg/2.5 cm) | 0.025 | 0.025 | 0.025 | 0.05 | 0.12 | 0.17 | 0.60 |
| | 0.02 | 0.02 | 0.025 | 0.07 | 0.11 | 0.20 | 0.55 |

Bakelite 180° Peel strength test

Peel strength was measured by coating each sample onto a PET strip 25 mm wide and 100 mm long and applying the strip to a bakelite plate. Then, a roller having a load of 300 g is rolled back and forth thereon to secure the sample to the plate. The sample is subsequently peeled off at an angle of 180° at a rate of 300 mm/min. to determine peel force. Unless otherwise specified, peel force is measured herein by this test.

The amount of plasticiser is one of the biggest factors that affect the physical properties of tape. In this case, a decrease in IMP clearly increases the peel strength of the tape.

(2) Amount of cross-linker

Table 25 summarises the formulation and peel strength of tapes, when the amount of cross-linker and IMP changes.

The amounts of plasticiser and cross-linker are as noted.

TABLE 25

| No. | 1 | 2 | 3 | 4 | 5 | 6 | 7 | 8 | 9 | 10 | 11 |
|---|---|---|---|---|---|---|---|---|---|---|---|
| Adhesive (g) | 1 | 1 | 1 | 1 | 1 | 1 | 1 | 1 | 1 | 1 | 1 |
| IPM (G) | 0.8 | 0.8 | 0.8 | 0.6 | 0.6 | 0.6 | 0.6 | 0.5 | 0.5 | 0.5 | 0.5 |
| Cross-linker (mg) | 4 | 3 | 2 | 3 | 2 | 1.5 | 1.25 | 3 | 2 | 1.5 | 1.25 |
| Peel strength (g/2.5 cm) | 27 | 25 | 40 | 47 | 55 | 70* | 80* | 47 | 63 | 97* | 107* |

*indicates that some adhesive remains on the bakelite after the test.

It can be seen that, when the amount of cross-linker decreases, the cross-linking density of the tape decreases, so that the softer adhesive has a greater peel strength.

The best combination of good peel strength and cohesion, in the above Table 25, are in the cases of adhesive 5 and 9.

EXAMPLE 14

Diethylene Triamine as Crosslinker

Adhesive B from Example 11 was used to prepare an oil-gel tape. The cross-linking conditions were as described in Example 12, but using diethylene triamine instead of adipic acid diamine. Diethylene triamine was dissolved in methanol to form a 2% w/w solution, and the amount of solution used contained 20 mg of this cross-linker.

The results are shown in Table 26.

TABLE 26

| Plasticiser | Properties | Thickness of adhesive (um) | Adhesion strength (g/25 mm) |
|---|---|---|---|
| Isopropyl myristate | (Soft and mild feeling) No residual adhesive when removed No paper removal | 700 | 30 |
| Methyl oleate | (Soft and mild feeling) No residual adhesive when removed No paper removal | 65 | 35 |

EXAMPLE 15

ISMN Patch

The adhesive from Example 10 was cross-linked in accordance with Example 12, except that diethylene triamine was used instead of adipic acid diamine, and that 0.1 g isosorbide mononitrate and 0.05 g glycerine monolaurate were added.

EXAMPLE 16

ISMN Patch (Comparative)

The same patch was prepared as in Example 8 except with no IPM.

EXAMPLE 17

Physical Properties

In vitro drug release, adhesion, and other physical properties for the adhesives of Examples 15 and 16 are summarised in Table 27 below.

TABLE 27

| | Property | Patch from Example 15 | Patch from Example 16 |
|---|---|---|---|
| 1 | Amount of ISMN released over 24 hours (mg/cm$^2$) on rat skin | 0.34 | 0.21 |
| 2 | Adhesion strength (g/25 mm) | 70 | 450 |
| 3 | Paper removal | No | Yes |
| 4 | Residual adhesive when removed | No | No |
| 5 | Reapplicability | Yes | No |

EXAMPLE 18

Testosterone Patch

The adhesive from Example 10 was cross-linked in accordance with Example 12, using 0.6 g IPM as plasticiser, except that 0.1 g testosterone and 0.05 g lauric acid diethanolamide were added.

EXAMPLE 19

Testosterone Patch (Comparative)

The same patch was prepared as in Example 18 except without IPM.

EXAMPLE 20

Physical Properties

In vitro drug release, adhesion, and other physical properties of the adhesives of Examples 18 and 19 are summarised in Table 28 below.

TABLE 28

| | Property | Patch from Example 18 | Patch from Example 19 |
|---|---|---|---|
| 1 | Amount of testosterone released over 24 hours (mg/cm$^2$) on rat skin | 1.03 | 0.77 |
| 2 | Adhesion strength (g/25 mm) | 90 | 650 |
| 3 | Paper removal | No | Yes |
| 4 | Residual adhesive when removed | No | No |
| 5 | Reapplicability | Yes | No |

EXAMPLE 21

Reapplicability Test

The adhesive from Example 10 was cross-linked in accordance with Example 12, using 0.6 g IPM as plasticiser. Bandage from Japanese Pharmacopoeia (Nichiban Co. Japan made) was used as a reference.

The tapes were applied to human forearm and after 30 minutes they were removed and adhesion strength was measured. The tapes were again applied to the different parts of forearm and after 30 minutes removed. This procedure was repeated three times.

The results are shown in Table 29 below.

TABLE 29

| | Adhesion strength (mg/25 cm) | | |
|---|---|---|---|
| Sample | First time | Second time | Third time |
| Oil gel | 50 | 45 | 45 |
| Nichiban bandage | 120 | 15 | 0 |

EXAMPLE 22

Hydroquinone Patch

The adhesive from Example 10 was cross-linked in accordance with Example 12, using 0.6 g IPM as plasticiser, except that hydroquinone of 0.15 g were added.

EXAMPLE 23

Hydroquinone Patch (Comparative)

The same patch was prepared as in Example 22, except without IPM.

EXAMPLE 24

Physical Properties

In vitro drug release, adhesion, and other physical properties are summarised in Table 30 below.

TABLE 30

| | Property | Patch from Example 8 | Patch from Example 9 |
|---|---|---|---|
| 1 | Amount of hydroquinone released over 24 hours (mg/cm$^2$) on rat skin | 3.2 | 0.4 |
| 2 | Adhesion strength (g/25 mm) | 75 | 450 |
| 3 | Paper removal | No | Yes |
| 4 | Residual adhesive when removed | No | No |
| 5 | Reapplicability | Yes | No |

EXAMPLE 25

Into a 2 liter glass vessel equipped with a stirrer, a heating device, a thermometer, and a reflux condenser, were introduced 232 g butyl acrylate, 226 g 2-ethylhexyl acrylate, 100 g diacetone acrylamide, 1.2 g tetraethylene glycol dimethacrylate, 30 g vinyl acetate, and 92 g methyl methacrylate. The solvent, consisting of 600 g ethyl acetate and 200 g toluene, was then added. Perhexa MC (0.1 g) was added to initiate polymerisation, and the solution was heated at 80° C. for 15 hrs.

A 21.7 g sample of the resulting solution (containing 10.0 g of adhesive polymer) was mixed with 5.0 g methyl oleate and 1.0 g 2% diethylene triamine/methanol solution, coated onto PET film, and heated at 80° C. for 20 minutes. The partially crosslinked adhesive layer was then covered with a PET release liner, and allowed to stand at 60° C. for 24 hrs to complete crosslinking. The sheet was then cut into tapes of 2.5 cm width and 10 cm length.

For the comparative sample, the same tape was prepared except with no plasticiser. Both tapes thus obtained (10×2.5 cm) were applied to the surface of a corrugated cardboard box. Then a roller of a load of 300 g was moved thereon back and forth to secure the adhesive sample to the surface. The samples were allowed to stand at room temperature for 2 weeks and then peeled off. The residual adhesive, paper removal, and adhesion strength were evaluated as follows.

| Sample | Phenomena at Peeling | Thickness of adhesive (um) | Adhesion strength (g/25 mm) |
|---|---|---|---|
| With plasticiser | No residual adhesive when removed<br>Not paper removal when removed<br>Reapplicable to corrugated cardboard box | 80 | 95 |
| Without plasticiser | No residual adhesive when removed<br>Paper removal when removed<br>Not reapplicable to corrugated cardboard box | 85 | 650 |

It can clearly be seen that the adhesives of the invention are useful for such applications.

What is claimed is:

1. An adhesive material suitable for use as a bioadhesive and comprising an adhesive polymer and a plasticiser therefor, wherein the adhesive is cross-linked, charaterised in that the adhesive polymer comprises ketone groups cross-linked by a polyamine cross-linking agent and wherein the plasticiser comprises between 17% and 200% w/w of the adhesive, and the adhesive is an acrylic block copolymer.

2. An adhesive according to claim 1, wherein the cross-linked ketone groups, prior to cross-linking, have substantially no tendency to enolisation.

3. An adhesive according to claim 1, wherein, prior to cross-linking, the keto form is at least 100 fold more stable than the enol form.

4. An adhesive according to claim 1, wherein, prior to cross-linking, the keto form is at least more stable than the enol form by a factor of $10^4$.

5. An adhesive according to claim 1, wherein, prior to cross-linking, the keto form is at least more stable than the enol form by a factor of $10^6$.

6. An adhesive according to claim 1, comprising alkyl acrylate and/or alkyl methacrylate monomer residues.

7. An adhesive according to claim 6, comprising; n-butyl acrylate, n-butyl methacrylate, hexyl acrylate, 2-ethylbutyl acrylate, isooctyl acrylate, 2-ethylhexyl acrylate, 2-ethylhexyl methacrylate, decyl acrylate, decyl methacrylate, dodecyl acrylate, dodecyl methacrylate, tridecyl acrylate or tridecyl methacrylate monomer residues, or any mixture thereof.

8. An adhesive according to claim 1, further comprising residues of a polar monomer.

9. An adhesive according to claim 8, wherein the polar monomer is hydroxyethyl acrylate, hydroxypropyl acrylate, vinyl pyrrolidone, acrylamide, dimethylacrylamide, acrylonitrile, diacetone acrylamide, vinyl acetate, or a mixture thereof.

10. An adhesive according to claim 1, wherein one or more ketone groups are provided by aliphatic, olefinically unsaturated keto monomer residues.

11. An adhesive according to claim 10, wherein said residues are residues of vinyl esters or allyl esters of aliphatic monobasic or diabasic acids containing a keto group.

12. An adhesive according to claim 1, comprising a combination of buryl acrylate, 2-ethylhexyl acrylate and diacetone acrylamide residues.

13. An adhesive according to claim 12, wherein said residues are in a ratio of 4:4:3.

14. An adhesive according to claim 1, wherein the plasticiser is isopropyl myristate or methyl oleate.

15. An adhesive according to claim 1, wherein the plasticiser comprises between 17% and 71% w/w of the adhesive.

16. An adhesive according to claim 1, wherein the plasticiser comprises between 37% and 62% w/w of the adhesive.

17. An adhesive according to claim 1, wherein the polyamine is a dialkyl triamine.

18. An adhesive according to claim 1, wherein the polyamine is diethylene triarnine or adipic acid diamine.

19. An adhesive according to claim 1, which is a block copolymer wherein the monomeric residues forming the hard section are selected from styrene, α-methylstyrene, methyl methacrylate and vinyl pyrrolidone, and mixtures thereof.

20. An adhesive according to claim 19, wherein the monomers are selected from styrene and/or polymethyl methacrylate.

21. An adhesive according to claim 1, having an adhesive strength such that, when applied as a tape, the tape can be applied to the skin and then removed without removing the stratum corneum layer of the skin surface.

22. An adhesive according to claim 21, which has an adhesive strength of 1.6 g/mm to 8 g/mm.

23. A tape comprising an adhesive according to claim 1.

24. A tape according to claim 23 for medical use.

25. A jotter note comprising an adhesive according to claim 1.

26. A transdermal patch comprising an adhesive according to claim 1.

27. A tape or patch comprising an adhesive according to claim 1, wherein the adhesive a drug or antimicrobial.

28. A tape or patch according to claim 27, wherein the contained substance is a substance exemplified in any of the accompanying Examples.

* * * * *